US012622776B2

(12) United States Patent
Katayama et al.

(10) Patent No.: US 12,622,776 B2
(45) Date of Patent: May 12, 2026

(54) CHOLECYSTITIS TREATMENT VIA GALLBLADDER OCCLUSION OR SEALING

(71) Applicant: OLYMPUS MEDICAL SYSTEMS CORP., Tokyo (JP)

(72) Inventors: Tomofumi Katayama, Kunitachi (JP); Takahiro Suzuki, Hachioji (JP)

(73) Assignee: OLYMPUS SYSTEMS CORP., Tokyo (JP)

( * ) Notice: Subject to any disclaimer, the term of this patent is extended or adjusted under 35 U.S.C. 154(b) by 582 days.

(21) Appl. No.: 18/170,840

(22) Filed: Feb. 17, 2023

(65) Prior Publication Data

US 2023/0270537 A1    Aug. 31, 2023

Related U.S. Application Data

(60) Provisional application No. 63/362,618, filed on Apr. 7, 2022, provisional application No. 63/268,545, filed on Feb. 25, 2022.

(51) Int. Cl.
*A61F 2/04* (2013.01)
*A61M 27/00* (2006.01)

(52) U.S. Cl.
CPC ............. *A61F 2/04* (2013.01); *A61M 27/002* (2013.01); *A61F 2002/041* (2013.01); *A61F 2220/0008* (2013.01)

(58) Field of Classification Search
CPC ................. A61F 2/04; A61F 2002/041; A61F 2002/045; A61M 27/002; A61B 17/1114; A61B 2017/00818
See application file for complete search history.

(56) References Cited

U.S. PATENT DOCUMENTS

| | | | |
|---|---|---|---|
| 8,460,314 B2 | 6/2013 | Kaji et al. | |
| 8,684,995 B2 * | 4/2014 | Sato ..................... | A61B 1/0014 600/101 |
| 2013/0090590 A1 * | 4/2013 | Young ................... | A61F 5/0076 604/8 |
| 2016/0317167 A1 | 11/2016 | Ben Muvhar | |
| 2017/0072173 A1 * | 3/2017 | Van Dam ............. | A61B 17/1114 |
| 2018/0280669 A1 * | 10/2018 | Shlomovitz ......... | A61M 27/002 |
| 2022/0167991 A1 * | 6/2022 | Miyamoto ........... | A61B 17/064 |
| 2023/0270537 A1 * | 8/2023 | Katayama ........ | A61B 17/12136 623/23.7 |
| 2025/0000634 A1 * | 1/2025 | Folan ................. | A61B 17/1114 |
| 2025/0072881 A1 * | 3/2025 | Flanagan ............. | A61L 24/104 |

* cited by examiner

*Primary Examiner* — Suzette J Gherbi
(74) *Attorney, Agent, or Firm* — Schwegman Lundberg & Woessner, P.A.

(57) ABSTRACT

A method comprises obstructing at least a portion of an inside of a gallbladder using a barrier, and suppressing, using the barrier, contacting at least a portion of an interior wall of the gallbladder with a bile from a cystic duct.

14 Claims, 9 Drawing Sheets

CHOLECYSTITIS TREATMENT VIA GALLBLADDER OCCLUSION OR SEALING

CROSS-REFERENCE TO RELATED APPLICATIONS

This application is based upon and claims the benefit of priority to U.S. Provisional Application Ser. No. 63/268,545, filed on Feb. 25, 2022, and U.S. Provisional Application Ser. No. 63/362,618, filed on Apr. 7, 2022, the entire contents of which is incorporated herein by reference.

FIELD OF THE DISCLOSURE

This document relates to systems, devices, and methods of cholecystitis treatment.

BACKGROUND

The gallbladder exists as a sac-like part in the bile duct system, which is a luminal organ.

Acute cholecystitis, which is one of the diseases of the gallbladder, often occurs when calculus generated in the gallbladder moves to a cystic duct.

The current standard of cholecystitis treatment is laparoscopic cholecystectomy, which invasively removes the gallbladder. In the laparoscopic cholecystectomy, there is no risk of recurrence because the gallbladder is removed, but there is room for improvement in terms of invasiveness to the patient because it is an invasive surgical procedure.

In the treatment of cholecystitis, a less invasive treatment method than laparoscopic cholecystectomy is being sought. U.S. Pat. No. 8,460,314 describes a method of puncturing the gallbladder from the gastrointestinal tract under ultrasonic endoscopy and eliminating the function of the gallbladder mucosa by cauterization or the like. By eliminating the function of the gallbladder mucosa, bile is not concentrated and the formation and growth of calculus are suppressed.

SUMMARY

This document describes, among other things, systems, devices, and methods of cholecystitis treatment, such as via gallbladder occlusion or sealing.

A method comprises obstructing at least a portion of an inside of a gallbladder using a barrier, and suppressing, using the barrier, contacting at least a portion of an interior wall of the gallbladder with a bile from a cystic duct.

A method of cholecystitis treatment comprises a removal step of removing contents of a gallbladder, and a bile suppression step of arranging a member in the gallbladder, and a sealing step of closing a gap between the member and the gallbladder, or between the member and a cystic duct.

DETAILED DESCRIPTION

A method of cholecystitis treatment according to a first embodiment of the present invention will be described with reference to FIGS. 1 to 8.

First, the contents of the gallbladder are removed in a removal step (step A). The contents of the gallbladder are mainly bile and gall calculus (calculus). The bile can be removed by passive or active (e.g., suction) gallbladder drainage, such as can include transporting bile from the gallbladder via a tube or stent or the like, and the calculus, if any, can be removed using various lithotripsy or extraction or other treatment tools. In an example, a portion of the tube can be placed at least partially within the cystic duct to drain or otherwise transport bile from the gallbladder via the cystic duct.

There are roughly two types of access routes to the gallbladder for performing gallbladder drainage, and in this embodiment, any route may be used.

Figure 1:
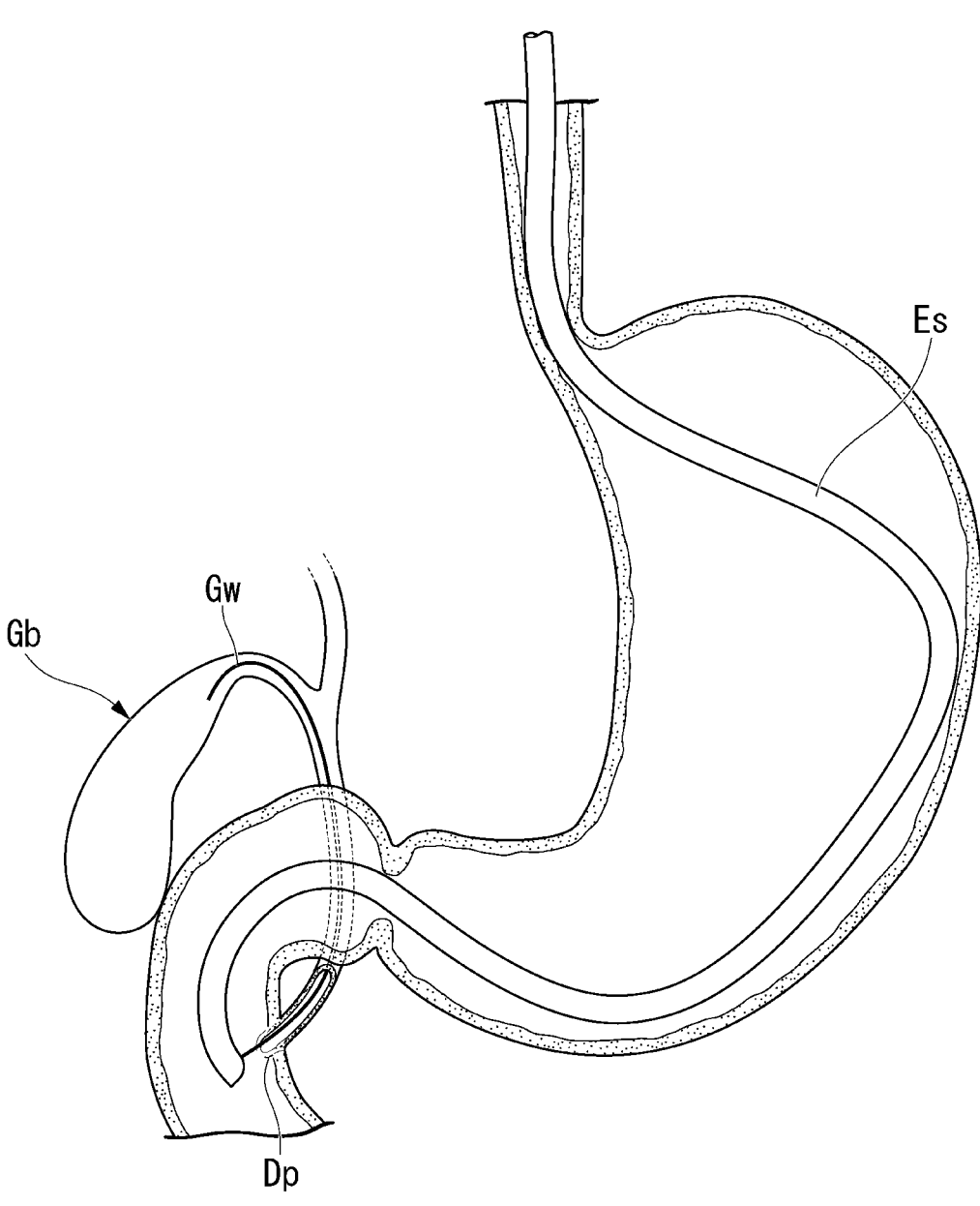
FIG. 1 is an illustration showing an example of an access operation to the gallbladder.

In the transpapillary access route (hereinafter, may be referred to as route A), as shown in FIG. 1, a guide wire Gw can be inserted into the duodenal papilla Dp from a distal portion of an endoscope Es introduced and located into the duodenum such as by a similar procedure as ERCP (endoscopic retrograde cholangiopancreatography). Then, the distal end of the guide wire Gw is brought into the gallbladder Gb, and the drainage tube is placed along the guide wire.

In the transperitoneal access route (hereinafter, may be referred to as route B), such as while confirming the position of the gallbladder with the image from the ultrasonic endoscope introduced into the duodenum, the puncture needle protruding from the endoscope is inserted into the duodenal wall and then inserted into the gallbladder. Then, with the puncture needle inserted in the gallbladder, the guide wire is passed through the puncture needle, the distal end of the guide wire is made to reach the inside of the gallbladder, and only the puncture needle is removed while leaving the guide wire in place. The drainage tube can be introduced and placed along the placed guide wire.

Figure 2:
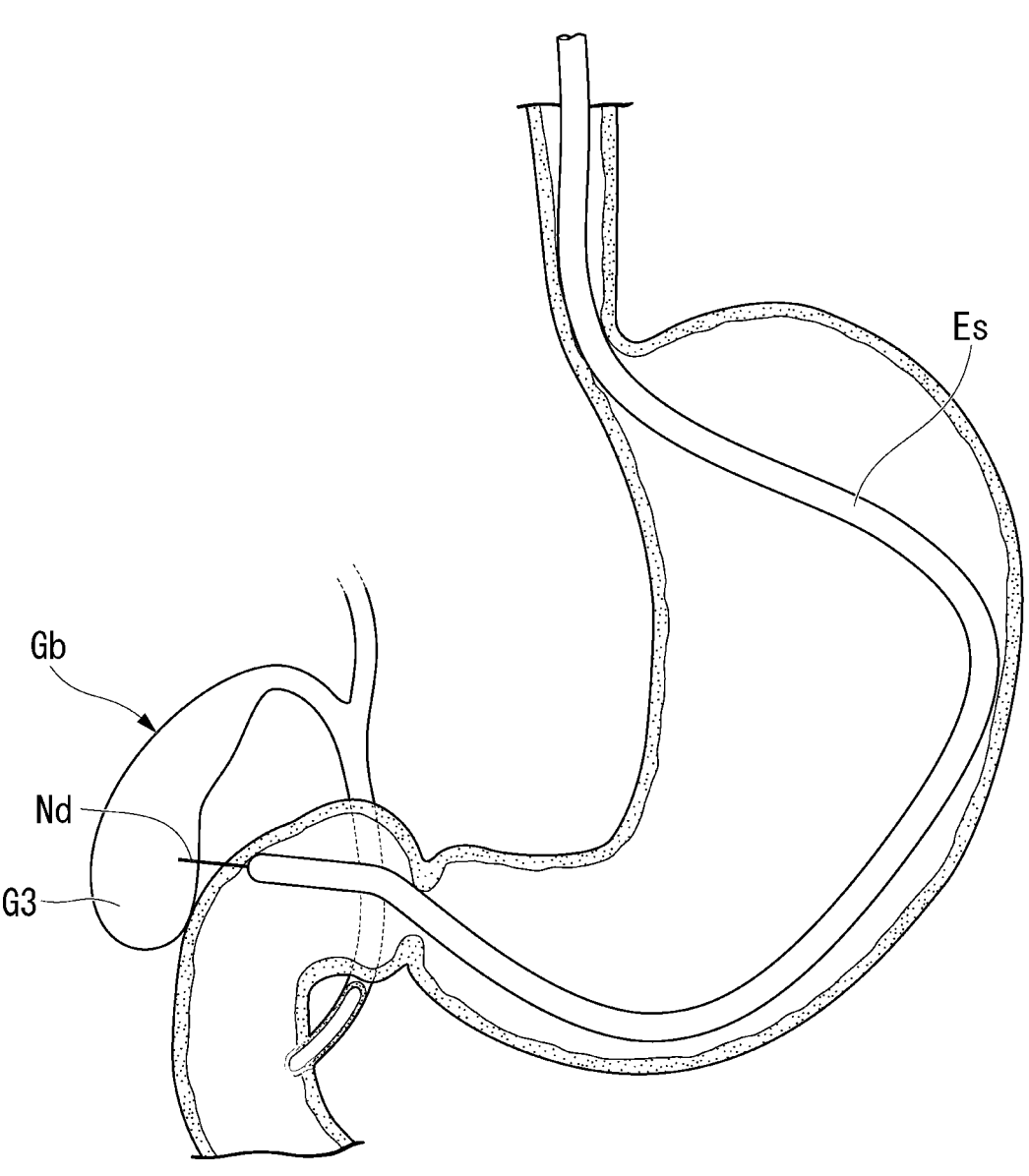
FIG. 2 is an illustration showing an example of an access operation to the gallbladder.

In route B, a drainage route may be established at any of the neck portion, body portion, and bottom portion of the gallbladder, but a drainage route may be established at the bottom portion in consideration of the subsequent procedure described later. When establishing a drainage route at the bottom portion, as shown in FIG. 2, a puncture needle Nd protruding from the endoscope Es can be inserted into a bottom portion G3 of the gallbladder Gb. With the puncture needle inserted in the gallbladder, the guide wire is passed through the puncture needle Nd, the distal end of the guide wire is made to reach the inside of the gallbladder, and only the puncture needle is removed while leaving the guide wire in place.

By the above procedure, a fistula, pore, port, or other communication hole that communicates the gallbladder and the duodenum is formed.

Figure 3:
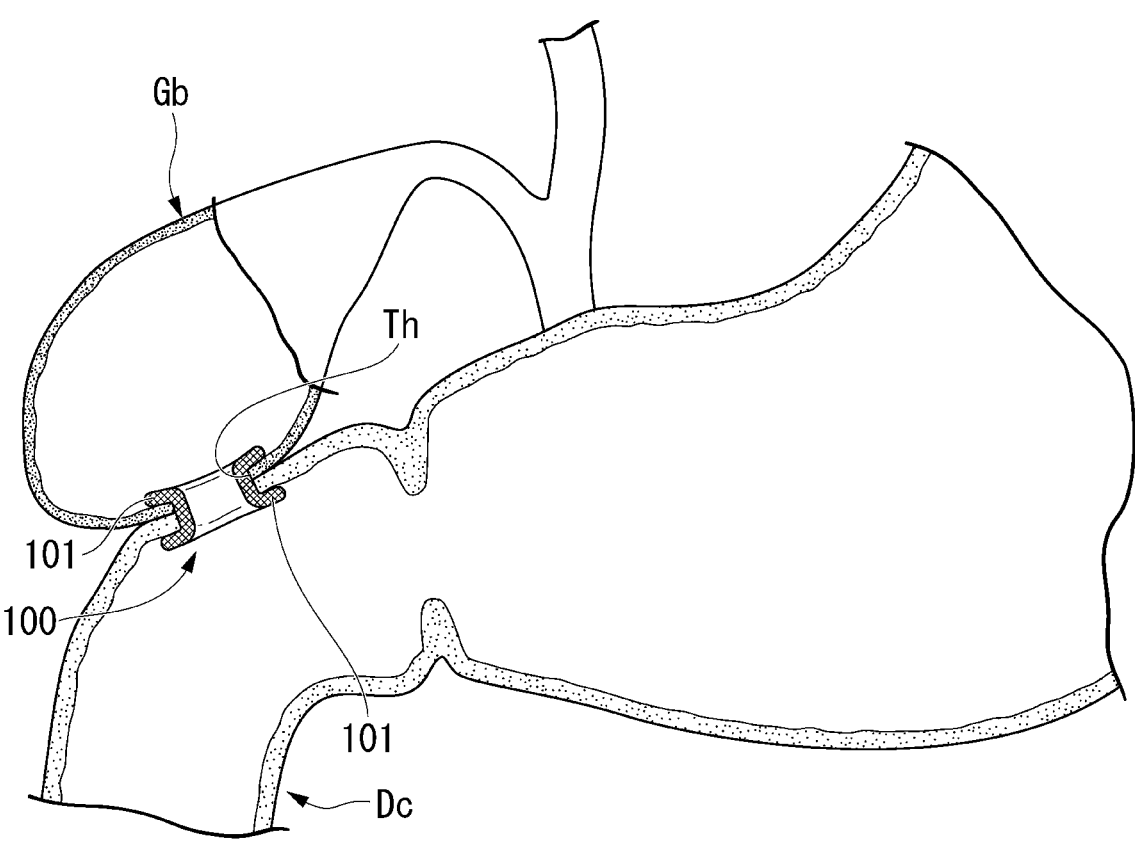
FIG. 3 is an illustration showing a state in which the gallbladder and the duodenum communicate with each other by a stent.

When route B is selected, the distal end of the stent or other treatment delivery device can be advanced to the gallbladder along the placed guide wire, and as shown in FIG. 3, a covered stent connecting the gallbladder and the duodenum is placed in a communication hole Th as a drainage tube, so that the communication hole Th can be stably opened with a sufficient size. A covered stent 100 such as shown in FIG. 3 has one or more flanges 101 such as on both sides in the axial direction of the tubular shape, and can be configured such as to anchor to or capture wall portions of the gallbladder Gb, the duodenum Dc, or both, such that it is difficult to become detached from the gallbladder Gb and the duodenum Dc after it is placed. A covered stent without the flange 101 can also be used, in which case the covered stent may be sutured or otherwise secured to the gallbladder or duodenum such as to help inhibit prevent it from becoming detached.

If there is calculus in the gallbladder after drainage is completed, the calculus can be removed as desired.

Calculus can be removed by various methods. Specific examples thereof include removal and crushing with a basket, removal by suction with a suction catheter, and crushing with a laser of a laser irradiation device. The calculus (stone) may be removed outside the gallbladder in its original form, e.g., in whole, or may be removed in a smaller size than the original form (e.g., in fractional portions) such as by crushing or otherwise fracturing or the like.

After removing the contents, the inside of the gallbladder may be washed such as with a physiological saline solution or using a drug solution such as containing an anti-inflammatory agent.

Next, a bile barrier such as a bag or sack (bile barrier member, member, coating, barrier) is installed in the gallbladder in a bile suppression step (step B).

Figure 4:
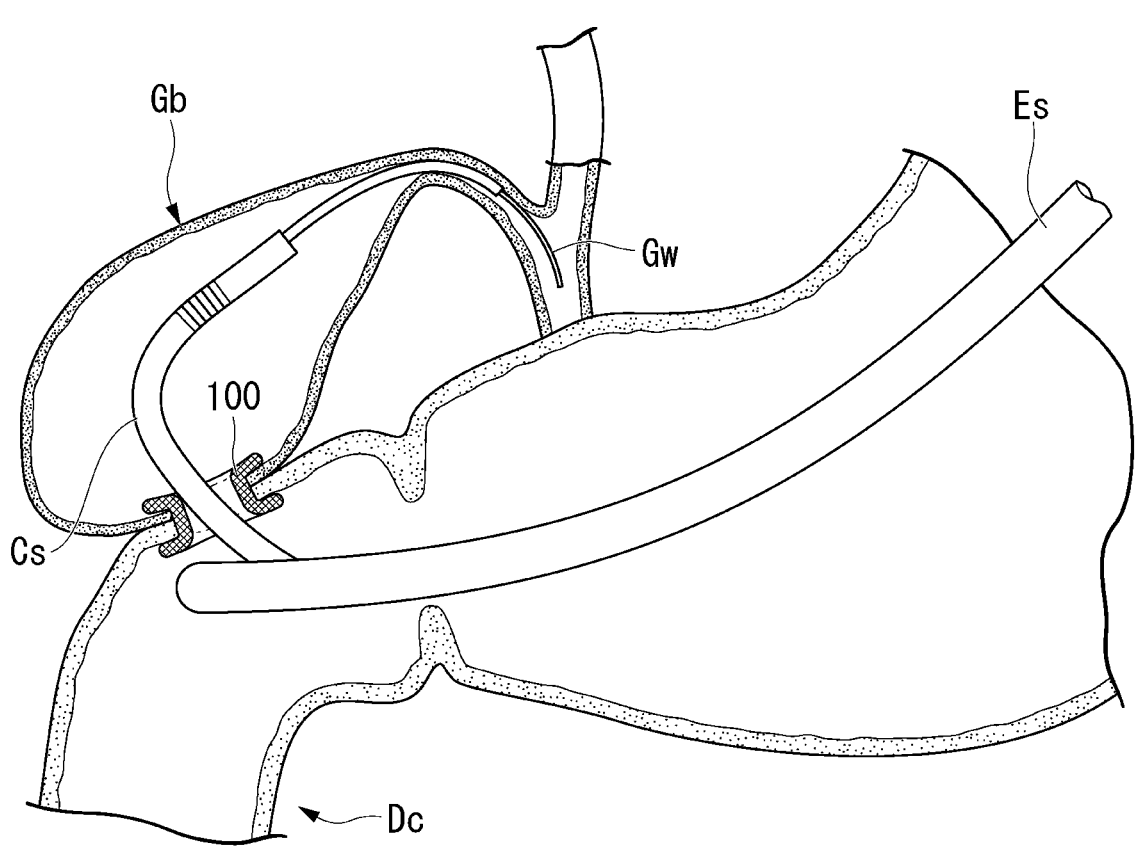
FIG. 4 is an illustration showing an example of a bile suppression step B according to a first embodiment of the present disclosure.
Figure 5:
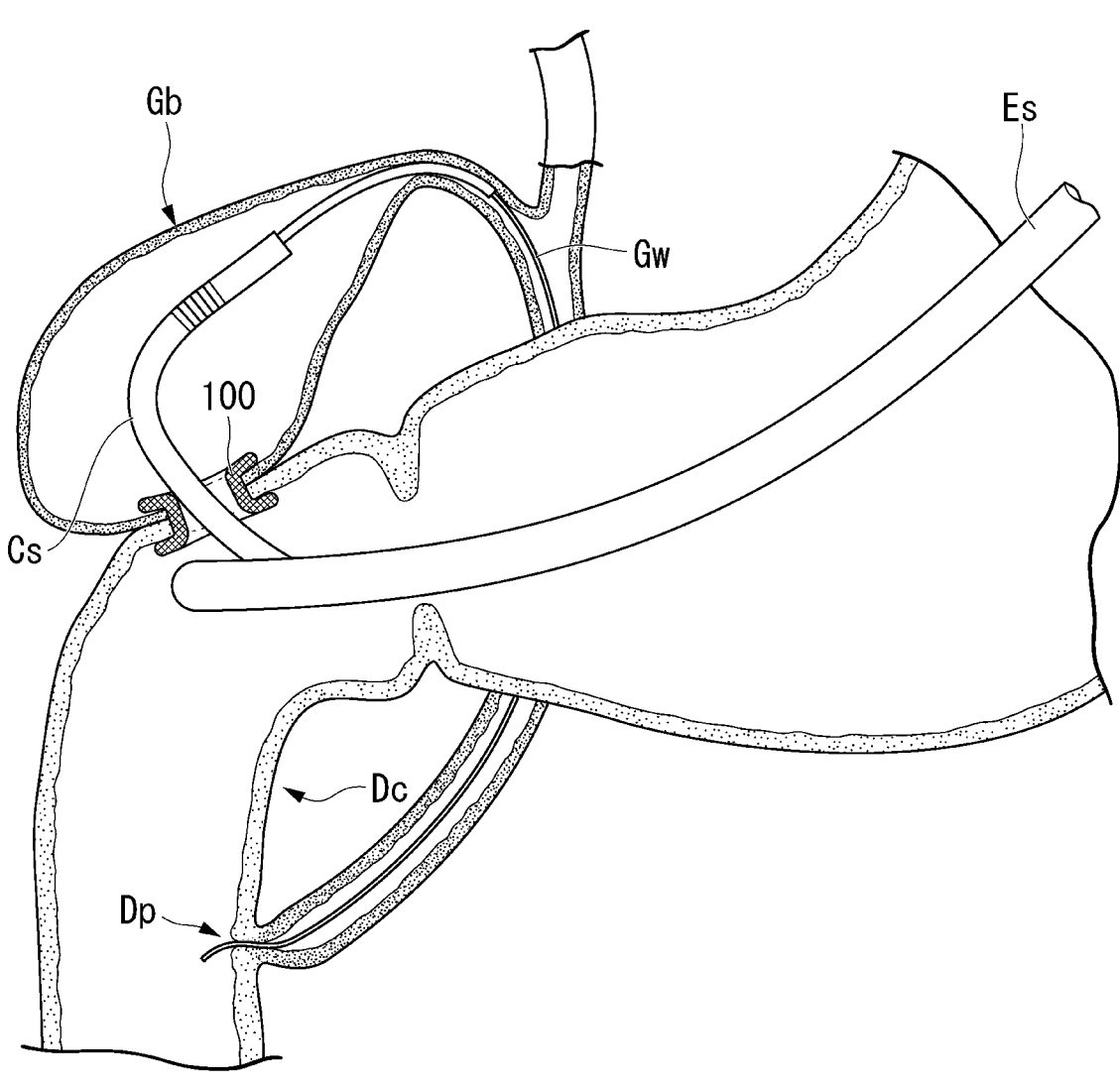
FIG. 5 is an illustration showing an example of a process of bile suppression step B.

FIG. 4 shows an example of the procedure of bile suppression step B when route B is selected. In FIG. 4, a bendable catheter or cholangioscope Cs is protruded from the treatment tool channel of the endoscope Es introduced into the duodenum Dc and inserted into the gallbladder Gb via the stent 100. Further, the guide wire Gw is protruded from the treatment tool channel of the cholangioscope Cs and inserted into the cystic duct from the inside of the gallbladder Gb. Further, the guide wire Gw is advanced into the common bile duct and protrudes from the duodenal papilla Dp such as shown in FIG. 5. The position of the distal end of the guide wire Gw in the bile duct can be confirmed by an X-ray fluoroscopic image or the like. The guide wire Gw does not necessarily have to protrude from the duodenal papilla Dp as long as it is placed in the common bile duct to a sufficient length.

When the guide wire Gw protrudes from the duodenal papilla Dp, the surgeon removes the cholangioscope Cs and the endoscope Es, leaving the guide wire Gw. Further, grasping forceps are inserted into the treatment tool channel of the endoscope Es, inserted into the duodenum again, and the guide wire Gw is grasped by the grasping forceps protruding from the endoscope Es. After that, when the grasping forceps are removed from the endoscope Es while the guide wire Gw is grasped, the guide wire protrudes from the forceps opening of the endoscope Es. Using the guide wire Gw as a guide, the delivery system of the bag or sack or other bile barrier can be inserted into the gallbladder duct via the duodenal papilla Dp and the common bile duct.

The delivery system, in an example, has a delivery catheter, a bile barrier bag or sack or pouch housed in the delivery catheter, and a pusher located behind the sack in the delivery catheter.

Figure 6:
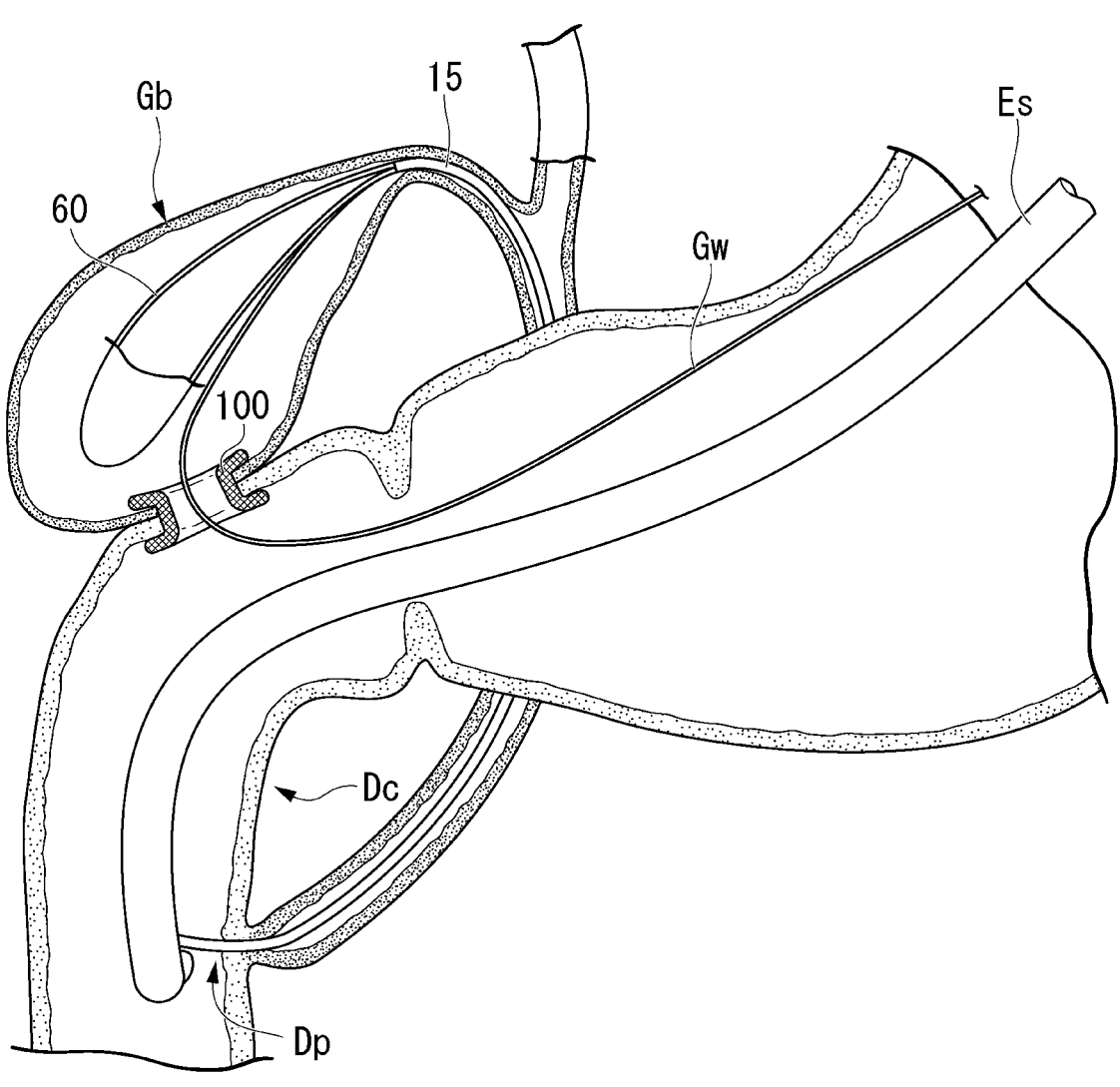
FIG. 6 is an illustration showing an example of a process of a bile suppression step B.

The surgeon inserts the delivery catheter from the cystic duct into the gallbladder and retracts the delivery catheter while supporting the sack 60 with the pusher. Then, as shown in FIG. 6, a bile barrier bag or pouch or sack (bile barrier member, member, coating, barrier) 60 is placed in the gallbladder. The surgeon moves the entire sack 60 out of a delivery catheter 15 with the opening of the sack 60 located inside the gallbladder duct. At this time, if an air supply lumen to the sack 60 is installed in the delivery catheter 15, the sack 60 can be brought closer to the gallbladder wall by supplying air from the air supply lumen when the sack 60 is placed in the gallbladder.

Next, the gap between the opening of the sack 60 and the inner wall of the bile duct is closed in a sealing step (step C).

Sealing step C can be performed in several ways.

Figure 7A:
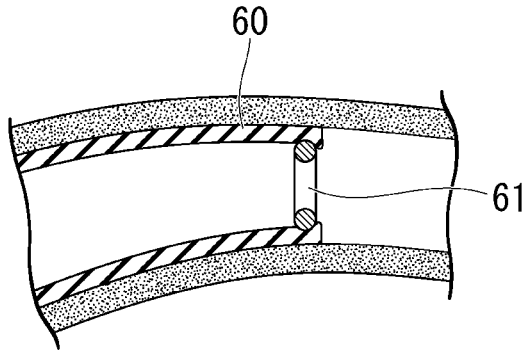
FIG. 7A is an illustration showing an example of an opening of a sack after a sealing step C.

In FIG. 7A, a self-expandable ring 61 is placed or fixed or attached in the opening of the sack 60, such as to help maintain patency of the opening of the sack 60. The ring 61 may be attached to the sack 60 in advance, or may be prepared separately from the sack 60. When attached to the sack 60, the ring is placed together with the sack 60 via the delivery catheter 15, and when prepared separately from the sack 60, the ring is placed via the delivery catheter 15 after the sack 60 is placed.

The ring 61 may be placed after the sack 60 has been inflated. In this case, since the opening extends and comes into contact with the wall of the cystic duct, the ring 61 can be easily placed.

Figure 7B:
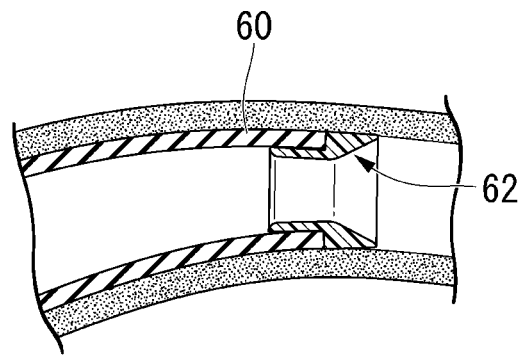
FIG. 7B is an illustration showing an example of an opening of a sack after a sealing step C.

In FIG. 7B, the opening of the sack 60 is covered with an adhesive 62 to join the opening and the cystic duct. When the adhesive 62 is used, it may be applied to the outer surface of the sack, or the inner wall of the gallbladder may be joined to the sack. When the adhesive 62 is used, for example, the delivery catheter 15 may be removed after the sack 60 is placed, another catheter or the like may be inserted, and the adhesive 62 may be applied to the opening position of the sack.

Figure 7C:
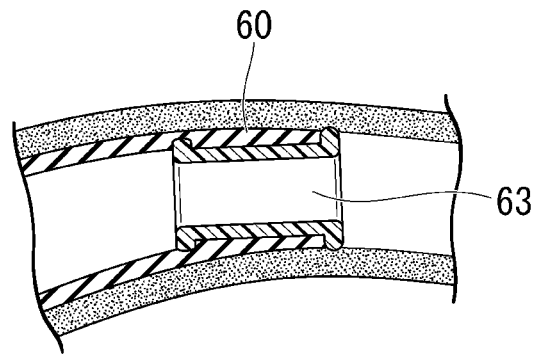
FIG. 7C is an illustration showing an example of an opening of a sack after a sealing step C.

In FIG. 7C, a stent 63 is placed in the opening of the sack 60. A self-expandable metal stent, a plastic stent, or the like can be suitably used as the stent 63. When the stent 63 is used, for example, the delivery catheter 15 may be removed after the sack 60 is placed, a stent delivery system or the like may be inserted, and the stent 63 may be placed at the opening position of the sack.

The stent 63 may be placed after inflating the sack 60. In this case, since the opening extends and comes into contact with the wall of the cystic duct, the stent 63 can be easily placed.

Regardless of which method described above is adopted, the gap between the opening of the sack and the inner wall of the bile duct is closed in a sealing step C, thus helping inhibiting or preventing from entering and contacting the interior wall of the gallbladder. When the sealing step C is executed, the opening may be sufficiently extended so that the wrinkles formed in the opening do not form a gap.

After the completion of the sealing step C, the guide wire Gw is removed together with the delivery system and the endoscope Es, and a series of procedures is completed. The stent 100 can be removed after an appropriate time.

Figure 8:
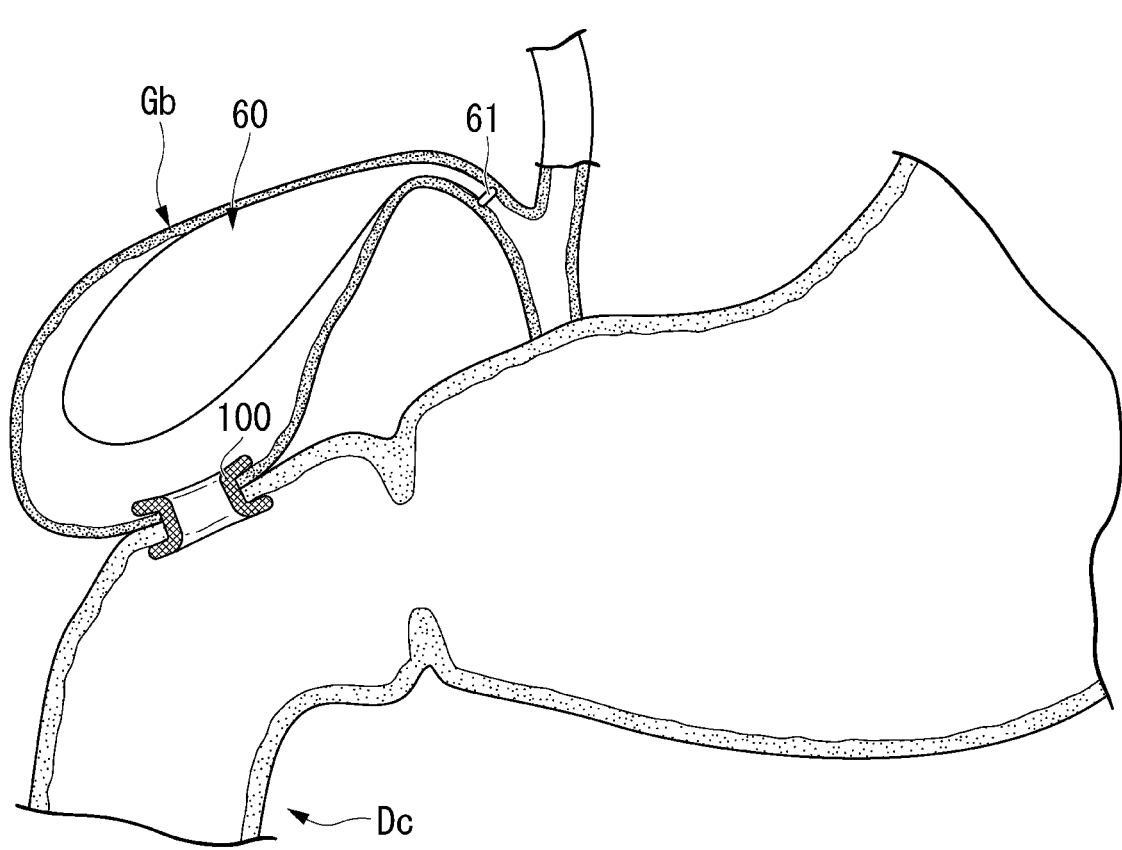
FIG. 8 is an illustration showing a state in which a bile barrier such as a sack is placed in the gallbladder.

In the present embodiment, as shown in FIG. 8, the sack 60 is placed in the gallbladder Gb in a state where the gap between the opening and the gallbladder is closed in the gallbladder duct (FIG. 8 shows an example in which the ring 61 is placed).

When the sack 60 is placed, the bile that travels from the liver to the cystic duct via the common hepatic duct flows into the sack 60, so that the bile does not come into contact with the inner wall of the gallbladder and is not concentrated by the gallbladder. In addition, the gap between the opening and the cystic duct is also closed, so that the bile does not flow into the gallbladder through between the sack and the wall of the cystic duct. Therefore, the formation and growth of calculus do not occur, and the recurrence and relapse of cholecystitis are suitably suppressed.

As described above, the method of cholecystitis treatment according to the present embodiment can suitably suppress the recurrence or relapse of cholecystitis without removing the gallbladder. Therefore, the invasiveness of the cholecystitis treatment to the patient can be significantly reduced, such as compared with laparoscopic cholecystectomy.

In the example of the sealing step B described above, since the delivery system is passed through the gallbladder duct using a guide wire protruding from the gallbladder to the duodenal papilla, the required skill level is not so high, and there is an advantage in that many surgeons can perform it. Alternatively, as another method of sealing step B, after performing the removal step A on route A, the used device may be removed leaving the guide wire and the remaining guide wire may be used to pass the delivery system through the gallbladder duct. Route A may involve a high degree of skill in the placement of the guide wire Gw shown in FIG. 1, but there is an advantage in that the placement of the stent 100 can be omitted by using this method.

In the treatment method according to the present embodiment, the purpose can be achieved if the bile barrier bag, balloon, pouch, or other sack can prevent contact between the bile and the gallbladder wall. Therefore, the size of the sack is not particularly limited and may be about the same size as the gallbladder, or may be smaller than the gallbladder. Furthermore, even if the size is the same as that of the gallbladder, the sack and the gallbladder do not need to be in contact with each other, so that they do not need to be inflated to the same size.

As the material of the bile barrier, e.g., bag, pouch, balloon, sack or the like, a biocompatible material such as silicone can be used, for example. The bile barrier may be formed in situ, within the gallbladder, such as by introducing a coating or covering that adheres or otherwise conforms to an interior wall of the gallbladder, such as throughout the entire interior volume of the gallbladder. Such coating or covering can also extend into the cystic duct.

The second embodiment of the present disclosure will be described with reference to FIG. 9. In the following description, the same reference numerals will be given to the configurations and the like that are common to those already described, and similar overlapping description will be omitted, for brevity.

In this embodiment, a bile barrier balloon is used as a member that helps inhibit or prevent or suppress contact between the inner wall of the gallbladder and the bile. Therefore, in a bile suppression step B, a gas or liquid or other fluid-inflated balloon is placed in the gallbladder.

Bile removal step A can be performed in the same manner as in the first embodiment.

In bile suppression step B, the bile barrier balloon delivery system is inserted into the gallbladder instead of the bile barrier sack delivery system.

After placing the balloon in the gallbladder, fluid such as air or saline is supplied into the balloon to inflate the balloon. The balloon is inflated to approximately the size of the interior spatial volume within the gallbladder, e.g., a volume that would otherwise be occupied by bile or other contents of the gallbladder.

When the balloon inflation fluid supply is finished, the balloon inflation supply means can be withdrawn from the balloon. The balloon can be kept inflated by a check valve, plug, seal, or the like.

When the device other than the balloon is removed, a series of procedures according to this embodiment is completed.

Figure 9:
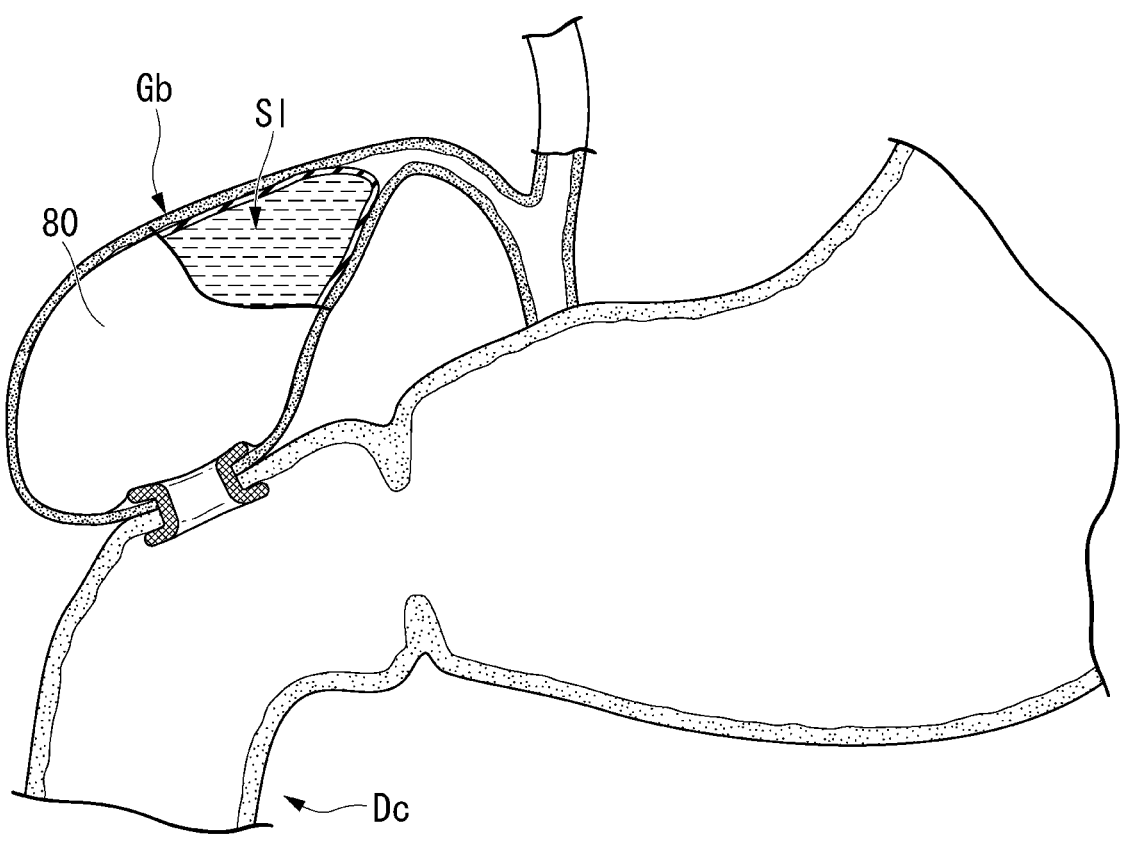
FIG. 9 is an illustration that shows an example of a state after completion of a treatment method according to a second embodiment of the present disclosure.

FIG. 9 shows an example of the state after the completion. In this example, a balloon 80 filled with physiological saline S1 as a fluid and inflated to an outer shape similar to that of the lumen of the gallbladder Gb, such as was previously occupied by bile and/or other contents, such that the bile barrier balloon is placed so as to fill the inside of the gallbladder Gb with almost no gap. Since most of the inner wall of the gallbladder Gb is covered in contact with the balloon 80, contact with bile may be inhibited or prevented, and recurrence or relapse of cholecystitis may be suppressed.

In this embodiment, sealing step C is not always necessary because almost all of the inner wall of the gallbladder is in contact with the balloon, but in order to more reliably prevent contact between bile and the inner wall of the gallbladder, the cystic duct may be blocked with an adhesive. Alternatively or additionally, a part of the balloon may be shaped so as to be able to enter the gallbladder, and the gap between the portion that has entered the gallbladder and the gallbladder may be closed with an adhesive, a plug, a check-valve, a seal, or the like.

Further, the bile barrier balloon does not necessarily have to be introduced into the gallbladder from the cystic duct, and may be introduced into the gallbladder via the stent 100. In this case, it is not necessary to use a guide wire for balloon placement, which can be done very easily. In this case, the stent 100 may be removed after the balloon is placed, or may be left in the gallbladder. If the stent 100 is left in place, even if bile flows into the gallbladder, the bile is discharged into the duodenum through the stent 100, so that concentration in the gallbladder is not performed and the risk of cholecystitis can be reduced.

Although each embodiment of the present invention has been described above, the technical scope of the present disclosure is not limited to the above embodiment. It is possible to change the combination of components, make various changes to each component, and delete them without departing from the teachings of the present disclosure. In addition to the changes described above, some additional changes are exemplified, but these are not limited all, and other changes are possible. Two or more of these changes may be combined as appropriate, or may be combined with the changes described above.

In the sealing step C, the gap between the inner wall of the gallbladder and the sack or balloon may be closed in place of or in addition to the cystic duct. In this case, for example, an adhesive is injected into the gallbladder between removal step A and bile suppression step B with a catheter or the like, and a sack or balloon is placed after the catheter is removed. The sack or balloon may then be inflated with fluid and glued to the inner wall of the gallbladder.

In the treatment method according to the present disclosure, it is not essential to clean the inside of the gallbladder. However, by thoroughly cleaning the inside of the gallbladder after physical or chemical treatment, the remaining tissue, bile, and drugs can be sufficiently discharged, providing advantages such as the tightness of the gallbladder being strengthened, and cholecystitis due to residual bile being inhibited prevented by keeping the gallbladder in close contact in a clean state.

In the treatment method according to the present disclosure, it is not essential to place a stent in the communication hole. For example, the communication hole formed by puncture may be temporarily expanded with a balloon or the like and passed through an endoscope or a biliary tract.

Although different from any of the above-described embodiments, after the completion of removal step A, a fluidized silicone or other hardenable or curable agent can be introduced into the gallbladder and cured to form a mass (bile barrier member, member, solid mass, coating, barrier) of a curing agent having the same degree as the lumen of the gallbladder, which allows bile suppression step B to be performed. In this method, most of the inner wall of the gallbladder Gb is in contact with and covered with a solidified mass of the curing agent, so that contact with bile may be prevented, and recurrence or relapse of cholecystitis may be suppressed. Even in this method, the sealing step C is not always necessary.

In this method, the gallbladder may be filled with silicone to the extent that the gallbladder is almost filled with silicone.

The substance to be filled is not limited to silicone as long as it can be introduced into the gallbladder in a fluid state and can be cured in the gallbladder. For example, two-component curing type or photocuring type epoxy adhesives and other curing agents such as acrylic adhesives can also be used.

1. A method of cholecystitis treatment comprises arranging a bile barrier member in a gallbladder; and using the bile barrier member, suppressing contact between an inner wall of the gallbladder and bile.

2. The method of cholecystitis treatment according to the example 1, wherein the bile barrier member includes a sack, and the method further comprises a sealing step of closing a gap between an opening of the sack and the gallbladder, or between the opening of the sack and a cystic duct.

3. The method of cholecystitis treatment according to example 2, wherein the sealing step comprises arranging a ring within the opening.

4. The method of cholecystitis treatment according to example 2, wherein the sealing step comprises joining between the opening and the gallbladder, or between the opening and the cystic duct.

5. The method of cholecystitis treatment according to example 2, wherein the sealing step comprises placing a stent in the opening.

6. The method of cholecystitis treatment according to example 1, wherein an outer shape of the bile barrier member is similar to a lumen of the gallbladder.

7. The method of cholecystitis treatment according to example 6, wherein the bile barrier member is a balloon filled with fluid.

8. The method of cholecystitis treatment according to example 6, wherein the bile barrier member is a solid mass of curing agent, and is introduced into the gallbladder in a fluid state.

The method of cholecystitis treatment according to example 1, wherein, the bile barrier member is introduced into the gallbladder using a guide wire inserted into a bile duct from the gallbladder and protruding from a duodenal papilla as a guide.

10. The method of cholecystitis treatment according to example 1, further comprising removing contents of the gallbladder.

11. A method of cholecystitis treatment comprises coating an inside wall of a gallbladder with a coating; and sealing at least one of an inside wall of a cystic duct and an inside wall of a gallbladder with the coating.

12. The method of example 11, comprising draining a bile from the gallbladder before the coating.

13. The method of example 13, wherein the draining comprises transporting bile from the gallbladder via a tube placed at least partially within the cystic duct.

14. The method of example any one of examples 11 or 13, wherein the draining further comprises:
    advancing a guidewire, via an endoscope having a distal portion located in a duodenum, from a duodenal papilla to the gallbladder; and
    placing a tube at least partially within the cystic duct using the guidewire.

15. The method of any one of examples 11 through 14, wherein the draining comprises:
    advancing a needle into the gallbladder through a duodenum via an endoscope having a distal portion located in the duodenum;
    advancing a guidewire from the endoscope to the gallbladder using the needle;
    retracting the needle into the endoscope; and
    placing a tube from the duodenum to the gallbladder using the guidewire.

16. The method of any one of examples 11 through 15, comprising:
    advancing a catheter and the coating from an endoscope to the gallbladder through a duodenal papilla;
    retracting the catheter to expose the coating.

17. The method of any one of examples 11 through 16, wherein the coating comprises:
    a bag configured to cover an inside of the gallbladder, the bag having an opening; and
    a ring fixed at the opening.

18. The method of example 17, wherein the sealing comprises:
    attaching the ring at least one of an inside of the cystic duct and an inside of the gallbladder.

19. The method of any one of examples 11 through 17, wherein the sealing comprises:
    applying an adhesive to an inside of the gallbladder.

20. The method of any one of examples 17 through 19, wherein the ring includes a stent.

21. The method of any one of examples 11 through 20, comprising:
    placing a balloon inside of the gallbladder.

22. The method of example 21, further comprising:
    inflating the balloon.

23. The method of any one of examples 21 or 22, wherein the sealing comprises:
    sealing an outside of the balloon and at least one of an inside of the cystic duct and an inside of the gallbladder.

24. A device for treating, inhibiting, or preventing cholecystitis, the device comprising:
    a bile barrier, configurable to be sized and shaped to contact an interior wall of a gallbladder to inhibit contact between bile and the interior wall of the gallbladder.

25. The device of example 24, wherein the bile barrier includes at least one of a bag or an inflatable balloon.

26. The device of any one of examples 24 or 25, wherein the bile barrier includes a hardenable bile barrier.

27. The device of example 26, wherein the bile barrier includes a hardenable bile barrier that is hardenable to be sized and shaped to occlude an interior of the gallbladder.

28. The device of any one of examples 26 through 27, wherein the bile barrier includes silicone.

29. The device of any one of examples 26 through 28, wherein the bile barrier includes a biocompatible fluid-impervious barrier material.

30. The device of any one of examples 24 through 29, wherein the bile barrier is configured to be sized and shaped to extend within and contact an interior wall of a cystic duct.

31. The device of any one of examples 24 through 30, wherein the bile barrier includes an opening.

32. The device of example 31, wherein the bile barrier includes a ring at the opening.

33. The device of example 32, wherein the ring is configured to maintain patency of the opening.

34. The device of any one of examples 24 through 33, in combination with at least one of a duodenoscope or other endoscope, a catheter, a drainage tube or stent or port, or a guidewire.

What is claimed is:

1. A method comprising:
obstructing at least a portion of an inside of a gallbladder using a barrier; and
suppressing, using the barrier, contacting at least a portion of an interior wall of the gallbladder with a bile from a cystic duct, wherein the barrier comprises a bag configured to cover an interior of the gallbladder, the bag having an opening.

2. The method according to claim 1, comprising draining a bile from the gallbladder before the obstructing, wherein the draining comprises:
transporting bile from the gallbladder via a tube placed at least partially within the cystic duct.

3. The method according to claim 2, wherein the draining further comprises:
advancing a guidewire, via an endoscope having a distal portion located in a duodenum, from a duodenal papilla to the gallbladder, and
placing a tube at least partially within the cystic duct using the guidewire.

4. The method according to claim 2, comprising draining a bile from a gallbladder before the obstructing, wherein the draining comprises:

advancing a needle into the gallbladder through a duodenum via an endoscope having a distal portion located in the duodenum;
advancing a guidewire from the endoscope to the gallbladder using the needle;
retracting the needle into the endoscope; and
placing a tube from the duodenum to the gallbladder using the guidewire.

5. The method according to claim 1, wherein the obstructing at least a portion of an inside of the gallbladder using a barrier comprises:
advancing a catheter and the barrier from an endoscope to the gallbladder through a duodenal papilla;
retracting the catheter to expose the barrier.

6. The method according to claim 1, wherein the barrier further comprises:
a ring fixed to the opening.

7. The method of claim 6, comprising attaching the ring to at least one of an inside of a cystic duct and an inside of the gallbladder.

8. The method according to claim 1, wherein the obstructing comprises:
applying an adhesive to an inside of the gallbladder.

9. A method of cholecystitis treatment, comprising:
a removal step of removing contents of a gallbladder;
a bile suppression step of arranging a member in the gallbladder, wherein the member is a sack; and
a sealing step of closing a gap between the member and the gallbladder, or between the member and a cystic duct.

10. The method of cholecystitis treatment according to claim 9, wherein
the member is inflatable, and
in the sealing step, the gap is closed by contact between the inflated member and the gallbladder, or the inflated member and the cystic duct.

11. The method of cholecystitis treatment according to claim 10, wherein in the sealing step, the gap between an opening of the sack and the gallbladder, or between an opening of the sack and the cystic duct is closed.

12. The method of cholecystitis treatment according to claim 11, wherein the sealing step comprises joining between the opening and the gallbladder, or between the opening and the cystic duct.

13. The method of cholecystitis treatment according to claim 11, wherein the sealing step comprises placing a stent in the opening.

14. The method of cholecystitis treatment according to claim 9, wherein, the member is introduced into the gallbladder using a guide wire inserted into a bile duct from the gallbladder and protruding from a duodenal papilla as a guide.

* * * * *